US009603680B2

(12) United States Patent
Antonini et al.

(10) Patent No.: US 9,603,680 B2
(45) Date of Patent: Mar. 28, 2017

(54) MEDICAL DEVICE FOR DENTAL PROSTHETIC SYSTEMS, A DENTAL PROSTHETIC SYSTEM, USE OF THE MEDICAL DEVICE AND A FORMING METHOD OF PROSTHETIC DEVICES

(71) Applicants: Matteo Antonini, Varese (IT); Alberto Salini, Lugano (IT)

(72) Inventors: Matteo Antonini, Varese (IT); Alberto Salini, Lugano (IT)

(*) Notice: Subject to any disclaimer, the term of this patent is extended or adjusted under 35 U.S.C. 154(b) by 229 days.

(21) Appl. No.: 14/380,463

(22) PCT Filed: Feb. 28, 2013

(86) PCT No.: PCT/IB2013/051607
§ 371 (c)(1),
(2) Date: Aug. 22, 2014

(87) PCT Pub. No.: WO2013/128406
PCT Pub. Date: Sep. 6, 2013

(65) Prior Publication Data
US 2015/0017603 A1   Jan. 15, 2015

(30) Foreign Application Priority Data
Feb. 29, 2012   (IT) .............. MI2012A0312

(51) Int. Cl.
*A61C 8/00*   (2006.01)
*A61C 13/08*   (2006.01)
(Continued)

(52) U.S. Cl.
CPC ............ *A61C 8/0068* (2013.01); *A61C 8/005* (2013.01); *A61C 8/006* (2013.01); *A61C 13/08* (2013.01); *C08K 3/005* (2013.01); *C08K 5/0058* (2013.01)

(58) Field of Classification Search
CPC ....... A61C 8/00; A61C 8/0016; A61C 8/0022; A61C 8/005; A61C 8/0068; A61C 8/006; A61C 13/08; C08K 3/05; C08K 5/0058
(Continued)

(56) References Cited

U.S. PATENT DOCUMENTS

| 744,291 A | * | 11/1903 | Carr | ..................... A61C 8/0086 |
| | | | | 433/169 |
| 4,182,034 A | * | 1/1980 | McCauley | ............... A61C 8/00 |
| | | | | 433/174 |

(Continued)

FOREIGN PATENT DOCUMENTS

CN       101014297        8/2007
DE       9316043 U1       1/1994
(Continued)

OTHER PUBLICATIONS

Transmittal of the International search Report and the Written Opinion of the International Searching Authority for PCT/IB2013/051607 mailed Sep. 10, 2013, 18 pages.
(Continued)

*Primary Examiner* — Nicholas Lucchesi
(74) *Attorney, Agent, or Firm* — Fish & Richardson P.C.

(57) ABSTRACT

A medical device (1) for dental prosthetic systems (2), the dental prosthetic system (2) being of a type comprising: a dental product (3) comprising a housing seating (6) longitudinally extending along a height of the dental product, an implant (5) destined to be installed in a seating made in a bone tissue of a maxilla or mandible of a patient, a fixing element (4) configured such as to insert in the housing seating and enabling engagement of the dental product (3) to the implant (5); the medical device (1) comprising a preformed solid body having a predetermined volume and an
(Continued)

elongate conformation configured such as to insert in the longitudinal housing seating (6).

20 Claims, 6 Drawing Sheets

(51) Int. Cl.
    *C08K 3/00*         (2006.01)
    *C08K 5/00*         (2006.01)

(58) Field of Classification Search
    USPC .................................................. 433/173, 174
    See application file for complete search history.

(56) References Cited

U.S. PATENT DOCUMENTS

| | | | | |
|---|---|---|---|---|
| 4,793,808 A | * | 12/1988 | Kirsch | A61C 8/0018 |
| | | | | 433/173 |
| 4,854,872 A | * | 8/1989 | Detsch | A61C 8/0001 |
| | | | | 433/173 |
| 4,907,969 A | * | 3/1990 | Ward | A61C 8/005 |
| | | | | 433/173 |
| 5,064,373 A | * | 11/1991 | Staubli | A61C 13/273 |
| | | | | 433/173 |
| 5,468,150 A | | 11/1995 | Brammann | |
| 5,803,735 A | * | 9/1998 | Gittleman | A61C 3/16 |
| | | | | 433/172 |
| 7,303,817 B2 | * | 12/2007 | Jia | A61K 6/0038 |
| | | | | 428/375 |
| 8,888,486 B2 | * | 11/2014 | Goodman | A61C 8/006 |
| | | | | 433/174 |
| 8,974,506 B2 | * | 3/2015 | Wenger | A61B 17/864 |
| | | | | 411/23 |
| 2005/0066854 A1 | | 3/2005 | Jia | |
| 2013/0288202 A1 | * | 10/2013 | Hochman | A61C 8/008 |
| | | | | 433/175 |
| 2014/0170597 A1 | * | 6/2014 | Honig | A61C 8/0053 |
| | | | | 433/173 |
| 2014/0205969 A1 | * | 7/2014 | Marlin | A61C 8/0001 |
| | | | | 433/173 |
| 2015/0282907 A1 | * | 10/2015 | Zipprich | A61C 8/0093 |
| | | | | 433/32 |

FOREIGN PATENT DOCUMENTS

| | | |
|---|---|---|
| KR | 100963432 B1 | 6/2010 |
| RU | 40885 | 10/2004 |
| WO | WO0185050 A2 | 11/2001 |
| WO | WO2004071327 A1 | 8/2004 |
| WO | WO2006022747 | 3/2006 |
| WO | WO2010106777 A1 | 9/2010 |
| WO | WO2011092681 A8 | 8/2011 |

OTHER PUBLICATIONS

Annex to for PCT/ISA/206, Communication Relating to the Results of the Partial International Search for PCT/IB/2013/051607 mailed Jul. 13, 2014, 3 pages.

* cited by examiner

MEDICAL DEVICE FOR DENTAL PROSTHETIC SYSTEMS, A DENTAL PROSTHETIC SYSTEM, USE OF THE MEDICAL DEVICE AND A FORMING METHOD OF PROSTHETIC DEVICES

CROSS-REFERENCE TO RELATED APPLICATIONS

This application is a National Stage under 35 U.S.C. §371 International Application No. PCT/IB2013/051607, having an International Filing Date of Feb. 28, 2013, which claims the benefit of IT Application No. MI2012A000312, filed Feb. 29, 2012. These applications are hereby incorporated by reference in their entirety.

FIELD OF INVENTION

The present invention relates to a medical device for use in the oral and dental surgery field, in particular in the field of implants. The invention further relates to a prosthetic system using the medical device, as well as a process for applying the medical device.

PRIOR ART

Implant rehabilitation is a surgical-prosthetic method for replacing one or more dental elements that have been lost and/or damaged. It is a reliable therapy, with a high success rate, and is accepted by the international scientific and professional community.

The lack of one or more dental elements involves a large number of the population, with consequent significant functional, personal and social problems. An implant therapy that has been successful leads to reacquiring ability in chewing and also a return to a satisfactory aesthetic level.

Implant-prosthetic restoration is made up of an implant (inside the bone, generally made of titanium) representing the part of the prosthetic system which engages to the maxilla or the mandible of the patient. Following the osteointegration of the implant, a prosthetic structure can be fitted which is essentially constituted by a dental product which stably engages a connecting element commonly known as an abutment. The connecting element or abutment and consequently the dental product are removably engaged to the implant thanks to a fixing element (generally a screw; this coupling is made possible by a connection, which on the basis of its position with respect to the implant is classified as internal or external and, from the morphological point of view, as polygonal (for example hexagonal, octagonal), not polygonal (multi-lobed) or conometric.

The connection between the abutment and the implant represents a crucial zone for the long-term function of implant-prosthetic rehabilitation; it also represents a point of discontinuity and weakness of the system. Ideally, in fact, this connection should also have the following requisites:
  precision, such as to guarantee a perfect coupling and a substantial continuity between the abutment and the implant,
  stability and resistance, such as to guarantee an adequate capacity to resist to chewing stress,
  absence of sites and efficient sealing between the abutment and the implant such as to minimise the possibility of formation and proliferation of bacteria; in fact, the eventual presence of discontinuities and the absence of seal would facilitate the proliferation of bacteria which, as known, can migrate towards the tissues surrounding the implant, causing drawbacks and pathologies of various kinds.

It should be noted that no matter how precise the manufacturing of the various components might be, it can never be perfect; in industrial production of mechanical components for the above-cited uses there is always the presence of dimensional tolerances in the order of +/−10 µm.

To this can be added the possibility that, during the chewing function, the abutment and the implant undergo elastic deformation and relative displacements; it is therefore clear how the prosthetic system described above exhibits a not insignificant number of problems. Further, as mentioned above, the abutment is fixed to the implant by means of a fixing element such as a through-screw. In order to be able to insert the screw in the abutment, the dental product has a housing seating which enables passage of the screw. Following the positioning of the screw the housing seating is sealed by the dentist using resins that are manually applied at the access opening at the housing seating. In some cases the resin is inserted in such a way as to occupy all the housing seating, which inevitably compromises the possibility of acceding in future to the through-screw and thus performing any maintenance activity of the prosthetic system. In other cases the housing seating is left pervious, or is filled with a filler material prepared on the spot, such as for example gutta-percha, cotton, Teflon, wax or another material: these methods are substantially ad hoc and are not such as to guarantee an adequate sterility of the area in which the operation is performed.

In other words, the solutions described and at present used can compromise the accessibility to the abutment-implant connecting screw and in any case do not allow either a perfect seal or an effective anti-bacterial action: it follows that areas susceptible to bacterial proliferation are left exposed, in particular at the housing seating of the through-screw. This can consequently determine a migration of bacteria at the level of the groove where the implant is installed and at the level of the gums, with a consequent inflammatory response of the organism, initially involving the peri-implantary soft tissues (mucosites), and then involving the hard support tissues (with the possibility of a reabsorption of the bone tissue, with a consequent loss of implant support—perimplantitis). In fact, the market at present offers no product or method which enables preventing the bacteria from colonising the internal part of the prosthetic components, with the consequences as described above.

AIM OF THE INVENTION

The aim of the present invention is therefore to obviate one or more of the drawbacks of the preceding solutions.

A first objective of the invention is to disclose a medical device and a prosthetic system that is simple to apply.

A further objective of the invention is to disclose a medical device, a prosthetic system and a method for applying the system that are able to limit or prevent the proliferation of bacteria.

A further aim of the invention is to disclose a medical device, a prosthetic system and method for applying the device which are such as substantially to prevent damage to functional and/or structural parts of the dental prosthetic system.

SUMMARY

One or more of the above-described aims and which will more fully emerge during the course of the following description are substantially attained by a medical device according to one or more of the accompanying claims.

Aspects of the invention are described in the following.

BRIEF DESCRIPTION OF THE DRAWINGS

Some embodiments and some aspects of the invention will be described in the following with reference to the appended tables of drawings, provided by way of non-limiting example in which.

DETAILED DESCRIPTION

With reference to the figures, 1 denotes in its entirety a medical device for use in oral and dental surgery, and more precisely in the field of implants. In particular, the dental device 1 is applicable in dental prosthetic systems 2 aimed at replacing, for functional and/or aesthetic reasons, the original dental set of a patient, where this has been lost or compromised.

Before describing the medical device 1 in detail, a brief description now follows of a dental prosthetic system 2, so as better to clarify the positioning and function of the medical device 1.

The prosthetic system 2 comprises an implant 5 configured such as to be engaged at the bone tissue of the maxilla or mandible of a patient. In the accompanying figures, an implant 5 is illustrated, in a non-limiting way, having a first constraining portion 14 defined by a threaded portion which enables a connection with the maxilla or mandible. The implant further comprises at least a second constraining portion 15 defined, non-limitingly, by a threaded hole which can removable engage at least a dental prosthesis after interposing of at least an appropriate mechanical connecting organ, as will be described in the following.

The implant 5 further comprises a centring portion 16 able to abut a respective centring counter-portion 17 of the prosthetic structure. The cooperation of the centring portions enables correctly positioning, in particular aligning, the dental prosthesis or the components on which the prosthesis is assembled with respect to the implant 5.

In the figures, an implant 5 is non-limitingly illustrated which exhibits a substantially cylindrical shape the first constraining portion 14 of which exhibits an external thread. The second constraining portion 15 exhibits a threaded hole which is arranged, non-limitingly, concentrically to the external thread. Note that the implants mostly used today are made of titanium due to the fact that this material offers an adequate mechanical performance and realises an excellent union with the bone tissues thanks to its characteristics of biocompatibility and osteo-integration.

In relation to the prosthetic structure it can be noted that it comprises at least a dental product 3 which is turn includes a connecting element or abutment 11 and an aesthetic portion 22 defining the external part destined to emerge from the gum and in this way re-establish the aesthetic and function continuity of the dental set. The aesthetic portion 22 and the abutment 11 can be re-assembled and solidly joined or couplable to one another during installation of the prosthetic system. The connecting element or abutment 11, also destined to emerge from the gum tissue of the patient, is interposed between the implant 5 and the aesthetic portion 22. The connecting element or abutment 11 is configured such as substantially to enable correct relative positioning between the implant 5 and the dental product 3 and such as to removably engaged to the implant 5.

In the illustrated examples, the connecting element 11 exhibits a first portion 12 unremovably engaged to the dental product 3 and a second portion 13 able to removably engage to the implant 5. In the figures, a connecting element 11 is illustrated that exhibits a substantially cylindrical shape developing between a first and a second end 11a, 11b. At the first end 11a, the connecting element 11 comprises the centring counter-portion 17 which non-limitingly comprises a projection able to removably engaged to the centring portion 16 of the implant 5 constituted by a seating that is substantially complementarily shaped to the projection of the connecting element or abutment 11.

As can be seen from the figures, the connecting element 11 is arranged substantially in the internal volume of the dental product 3. With the aim of facilitating the coupling between the aesthetic portion 22 and the abutment 11, the abutment can exhibit a constraining portion 18, at an external perimeter surface thereof. The constraining portion 18 is non-limitingly represented by at least a perimeter seating 19: this seating receives the material of the aesthetic portion and in fact defines an undercut able to axially block the aesthetic portion on the connecting element 11. As can be seen in the accompanying figures, the connecting element 11 further comprises an auxiliary constraining portion 19a able essentially to function as an anti-rotation element. In fact, the auxiliary constraining portion 19a comprises, non-limitingly, a flat or multi-faceted portion able to define, on the external surface of the abutment 11, at least an abutting plane predisposed to house the material of the dental product 3 and prevent rotation thereof with respect to the connecting element or abutment 11.

As for the internal part of the connecting element 11, it comprises a passage seating 20 extending along the entire development of the element 11 and in particular between the first and second end 11a, 11b. The passage seating 20 extends substantially parallel to the extension direction of the connecting element 11 and is in particular arranged at the centre thereof. The passage seating 20 can for example comprise a first and a second cylindrical portion connected to one another and aligned along the development of the abutment. The first cylindrical portion extends from the second end 11b of the connecting element 11 towards the first end while the second cylindrical portion extends from the first end 11a of the connecting element 11 towards the second end 11b. Note that the first and the second cylindrical portion exhibit a different diameter so that a support plane 23 is generated at a connecting zone between the two portions. In greater detail, the first cylindrical portion exhibits a greater diameter than the diameter of the second cylindrical portion.

The passage seating 20 is configured such as to receive internally thereof a fixing element 4 configured such as to removably engage the connecting element 11 and the implant 5. As can be seen from the accompanying figures of the drawings, the fixing element 4 non-limitingly comprises a screw: the head of the screw abuts against the support plane 23 generated by the cylindrical portion while the terminal thread of the screw cooperates with the second constraining portion 15 of the implant 5, creating in this way an axial block between the fixing element 11 and the implant 5.

As previously mentioned, the dental product 3 of the prosthetic structure further comprises an aesthetic portion 22, representing the external and exposed part of the system, which covers the abutment 11 up to the interface zone with the implant 5: in this way, once the screw is fixed to the implant, the aesthetic portion 22 emerges perfectly from the gum tissues, re-establishing the continuity of the patient's set of teeth and concealing both the implant and the connecting element or abutment 11.

Figure 3:
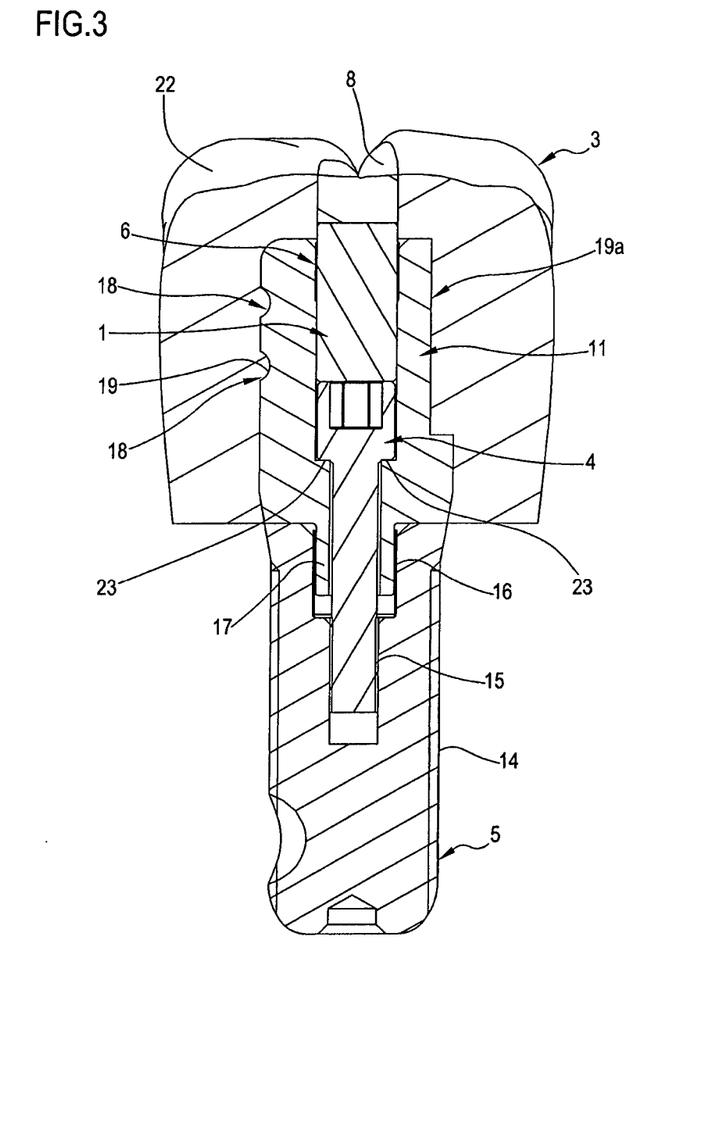
FIG. 3 is a transversal section of the dental prosthetic system according to a first embodiment.

FIG. 3 illustrates an embodiment of the dental product 3 in which the aesthetic portion 22 and the abutment 11 thereof are joined before the coupling of the abutment 11 to the implant. With the aim of guaranteeing the access by insertion of the fixing element, in the embodiment illustrated in FIG. 3 the aesthetic portion 22 of the dental product 3 comprises, non-limitingly, a passage seating 21 extending from an access opening 7 along the longitudinal development of the dental product 3, in particular along the height extension thereof. The passage seating 21 through the aesthetic portion 22, during the engagement between the portion 22 and the abutment 11, is aligned to the passage seating 20 thereof. In this way the passage seating 21 enables access from outside for insertion and if necessary removal of the fixing element 4 with respect to the whole dental product 3. The passage seatings 20, 21 of the dental product 3 define a longitudinal housing seating 6 configured such as to enable passage and to receive the fixing element 4. In greater detail, the longitudinal housing seating 6 extends from the access opening 7, arranged at an external surface of the dental product 3, along all the prosthetic structure, crossing the aesthetic portion 22 and the abutment 11. In use, following the insertion of the fixing element 4 internally of the housing seating 6, the housing seating is sealed at the external surface by means of a closing element 8.

In greater detail, the closing element 8 can comprise obturating material, for example in an acetal resin or an acrylic resin or in a compound resin. The closing element 8 is applied in such a way as not to occupy the whole internal volume defined by the housing seating 6 and installed in such a way that it can seal the access opening 7. In this last above-described condition, the medical device 1 is arranged internally of the housing seating 6 between the closing element 8 and the fixing element 4 (FIG. 3).

Figure 4:
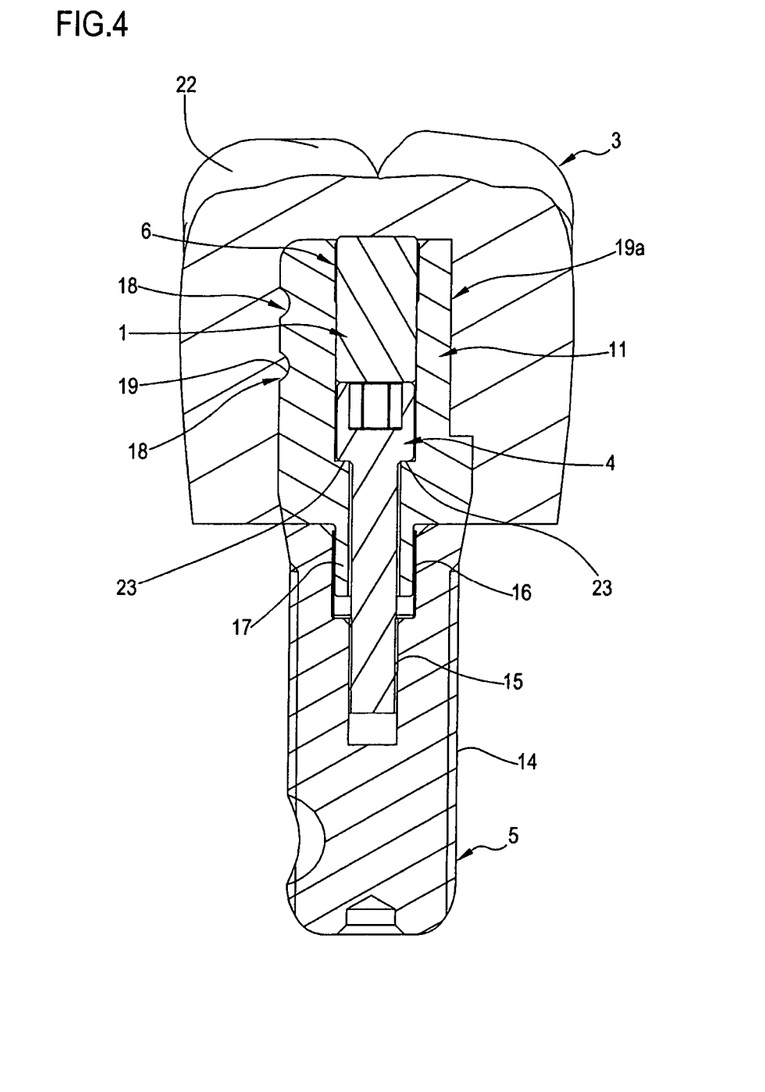
FIG. 4 is a transversal section of a dental prosthetic system according to a second embodiment.
Figure 5:
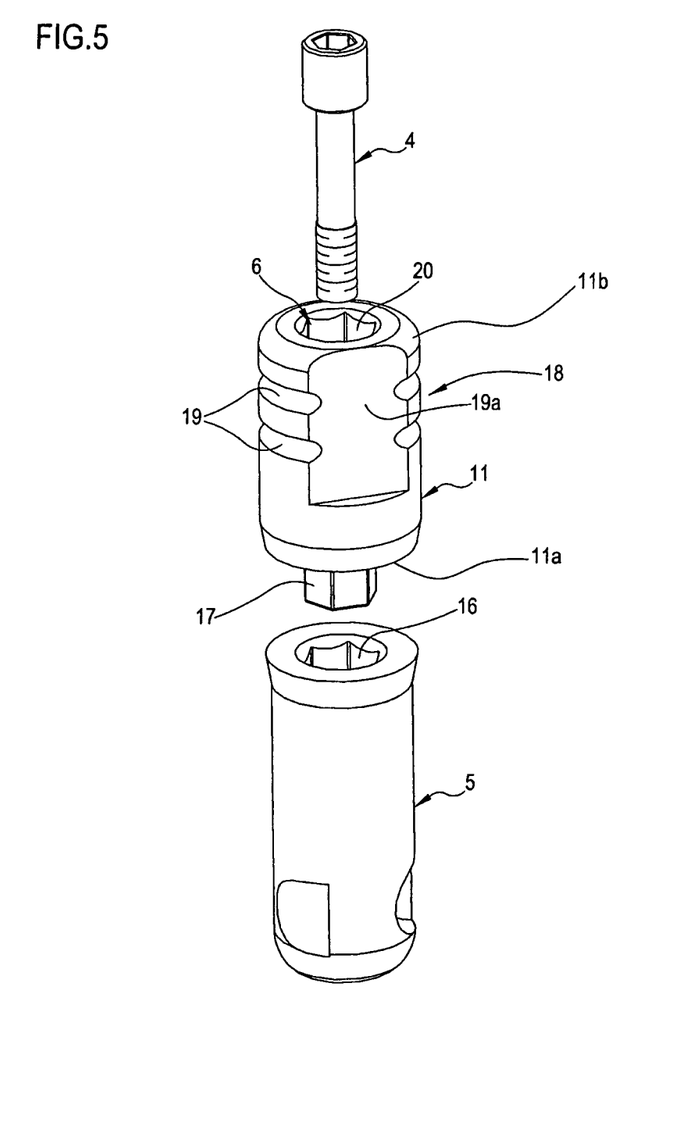
FIG. 5 is an exploded view showing an implant, a connecting element and a fixing element according to aspects of the present invention.

FIG. 4 illustrates a further embodiment in which the aesthetic portion 22 is coupled to the connecting element or abutment 11 following the engagement of the connecting element 11 with the implant 5. In greater detail, the fixing element 4 is in this case inserted into the connecting element 11 and engaged with the implant 5, before fixing the aesthetic portion 22. The aesthetic portion 22 defines a housing compartment complementarily shaped to the abutment and able to receive the connecting element 11. The fixing of the aesthetic portion 22 to the abutment 11 is carried out, subsequently to the fixing of the abutment and the insertion of the medical device 1 in the seating 6, thanks to the depositing of a resin or cement externally of the abutment and/or internally of the housing compartment. Following the positioning of the aesthetic portion 22 on the abutment 11, the resin or cement can engage the constraining portion 19 and the auxiliary constraining portion 19a of the abutment 11. With the solidification of the resin or cement, a coupling is guaranteed between the aesthetic portion 22 and the connecting element 22. In this last described condition, the aesthetic portion can exhibit a housing seating able to abut and at least partly receive the medical device 1. As mentioned, the device 1 in the example of FIG. 4 is inserted into the passage seating 20 of the abutment before the positioning and fixing of the aesthetic portion 22, thus being interposed between the fixing element 4 and the aesthetic portion 22.

In a more detailed analysis of the specific structure of the medical device 1, it can be seen that it exhibits a substantially elongate shape able to essentially occupy at least the entire axial volume of the longitudinal housing seating 6. In still greater detail, with reference to the embodiment of FIG. 3, the medical device 1 abuts on one side against the closing element 8 while on the other side it abuts the fixing element 4. Observing the embodiment of FIG. 4, the medical device 1 on one side abuts against an internal surface of the aesthetic portion 22 and on the other side against the head of the fixing element 4. The elongate conforming body of the medical device 1 extends along a prevalent development direction and the ratio between the extension of the body along the prevalent development direction and the maximum transversal volume of the body, measured perpendicularly to the prevalent development direction, is for example greater than 2, in particular greater than 8, still more in particular greater than 10. The medical device 1 can have different geometrical forms which however must enable an easy application internally of the longitudinal housing seating 6 of the fixing element 4. In a preferred embodiment, the medical device 1 exhibits a shape that is substantially complementary to the shape of the longitudinal housing seating 6. In this way, the medical device 1 essentially occupies both the axial volume and the transversal volume of the housing seating 6. The height of the device 1, measured along the prevalent development thereof is comprised between 10 mm and 50 mm (preferably the height can be 20 mm).

Figure 1:
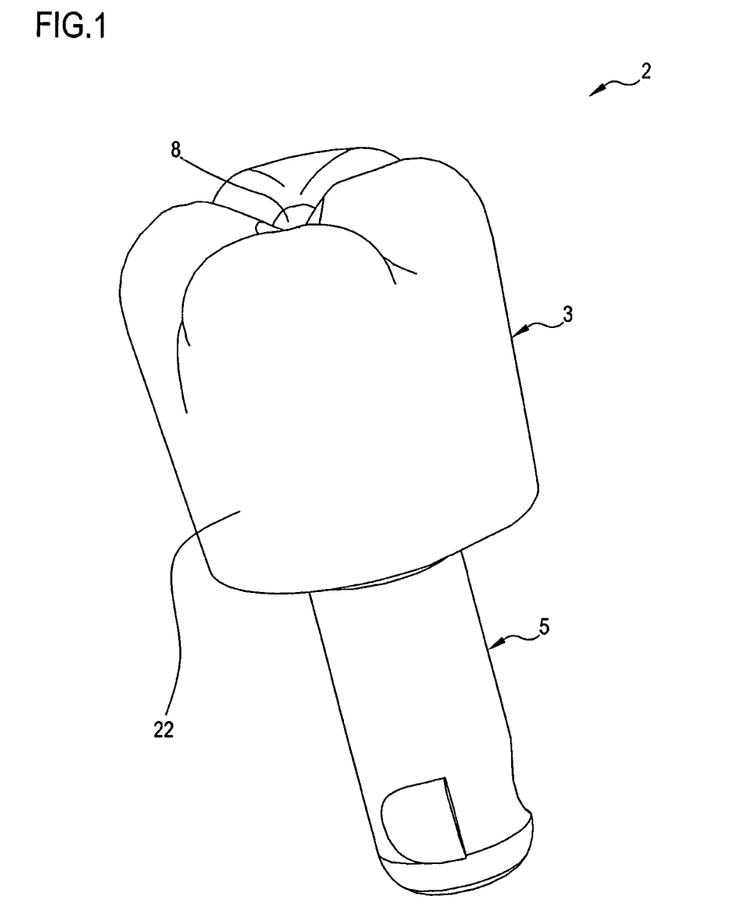
FIG. 1 is a perspective view of a dental prosthetic system according to the present invention.
Figure 2:
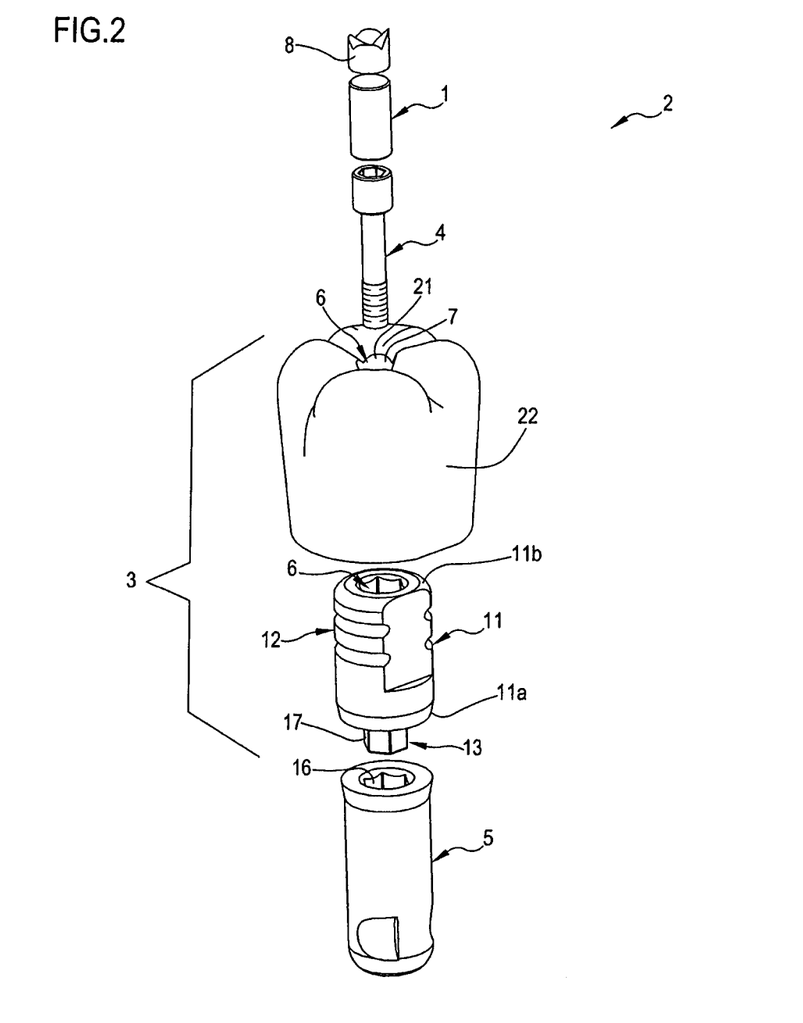
FIG. 2 is an exploded view of FIG. 1.

FIGS. 2, 3 and 4 illustrate a first embodiment of the medical device 1 exhibiting a complementarily shaped cylindrical shape to the shape of the housing seating 6. Alternatively, the housing seating 6 and the medical device can exhibit different shapes such as for example a conical, truncoconical or prismatic shape.

Figure 6:
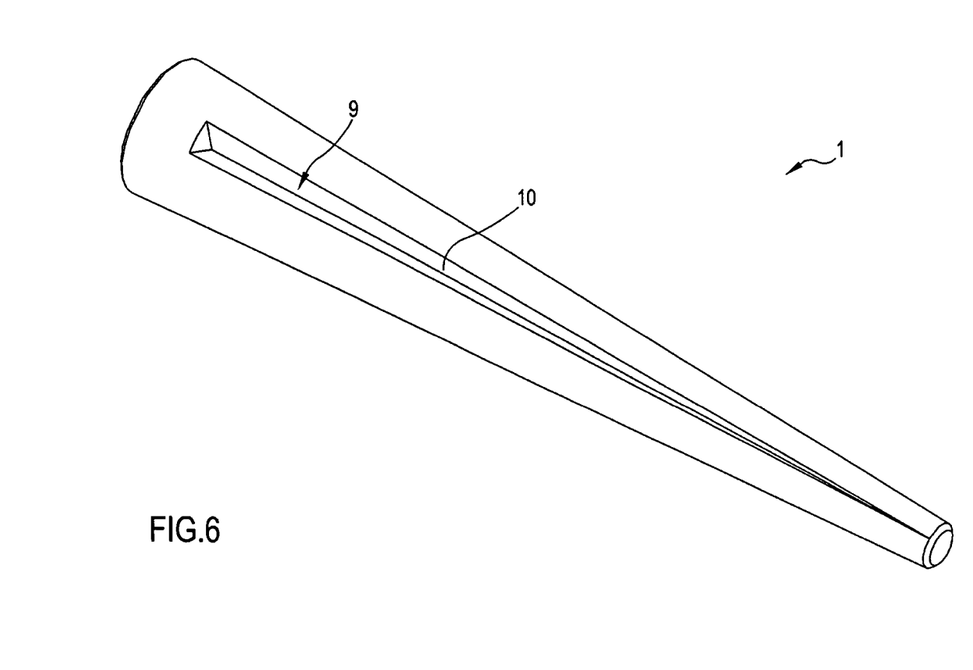
FIG. 6 is a perspective view of a medical device according to an aspect of the present invention.

FIG. 6 illustrates a further embodiment of the medical device 1 exhibiting a truncoconical shape, having for example the following dimensions: height, measured along the development of the medical device 1, comprised between 10 mm and 50 mm (preferably the height can be 20 mm). Again considering a case in which the medical device is truncoconical, the smallest diameter can be comprised between 0.001 and 2 mm, preferably less than 1 mm, while the largest diameter can be comprised between 0.5 mm and 10 mm, preferably greater than 3 mm. FIG. 6 illustrates an embodiment of the medical device 1 in which the body further comprises a recess 9 developing substantially parallel to the prevalent development direction of the device. As visible from the figures, the recess 9 exhibits, in a non-limiting way, a shape (see in cross-section) that is substantially V-shaped with the apex directed internally of the body. Alternatively the recess 9 can exhibit a profile (see in cross-section) that is substantially C-shaped, with the concavity facing towards the outside of the body.

The shape of the recess 9 enables a dimensional variation to the transversal size of the medical device 1 during an inserting condition thereof internally of the housing seating 6. In particular, the recess 9 defines an opening 10 on the medical device 1 which can exhibit a variable or constant width along the development of the device. FIG. 6 illustrates, non-limitingly, a condition in which the width of the opening 10 of the recess 9 varies substantially linearly along the development direction of the body. In still greater detail, the recess 9 is useful in cases in which there is a medical device 1 having a transversal size which in rest conditions is greater than the size of the longitudinal seating 6. In this regard note that a recess of the described type can also be fashioned on the device 1 which has a cylindrical or prismatic shape. Thanks to the recess 9, during the inserting of the body internally of the longitudinal housing seating 6, the recess itself enables a transversal contraction of the body of the medical device 1 enabling insertion thereof into the housing seating 6 and guaranteeing a certain elastic reaction against the surfaces delimiting the seating 6.

In further detail, the medical device 1 is defined by a preformed solid body having a predetermined volume and an elongate conformation configured such as to insert in the longitudinal housing seating 6.

The medical device 1 is formed starting from polymer or polymerisable material which is present in a weight percentage comprised between 80 and 99.5%, in particular between 92 and 97%, still more in particular between 93 and 95%.

In greater detail, the body of the medical device 1 is industrially obtained using classes of polymers such as thermosetting polymers or resins, for example: phenolic, amidic, epoxy, polyurethane, unsaturated polyester, silicone, alchidic. Alternatively the body of the medical device 1 can be realized using polymers or thermoplastic resins, such as for example: acrylic, polycarbonates, thermoplastic polyesters, vinyl-esters, vinyl polyfluorides, polyolefins (polyethylene, polypropylene). The polymer used for forming the medical device 1 can preferably comprise one or more polymers technically defined as Thermo Plastic Elastomers (TPE). The TPE preferably used to obtain the polymer matrix of the medical device of the invention is optionally selected such as to resist the corrosive attack, both acid and basic, on the environment of the oral cavity and the degrading action of the bacteria, both saprophyte and pathogens, present in the oral cavity. The TPE preferably used in the present is available, for example, under the Thermolast M mark and, on the date of filing of the present application, by the company Kraiburg TPE GmbH & Co.KG. In particular, the material realized by Kraiburg TPE GmbH & Co.KG and preferably used is marketed at present with the code TM7LFT.

If a polymerisable material is used it is possible to perform the step of polymerization (hardening), obtained with or without chemical or physical catalysers, of the polymer matrix before or after the insertion of the medical device 1 internally of the housing seating 6.

Active agents can also be added to the polymer or polymerisable matrix of the medical device of the invention; for example the active agents can be selected from among antibacterial agents, antiviral agents, antifungal agents, biocidal agents, bacteriostatic agents, either singly or in association. The active agents are preferably characterized by a very low or in any case insignificant solubility in water such as to limit as far as possible over time a reduction of the concentration thereof in the device and therefore their activity, for example due to saliva. The biocidal agent is preferably present in the medical device 1 with a weight percentage comprised between 0.1 and 5%, in particular between 0.5 and 2%, still more in particular between 0.7 and 1.5%. The biocidal agent is structured in micro-particles the dimensions of which are comprised between 0.5 and 30 µm, in particular between 2 and 7 µm, still more in particular between 3 and 5 µm. The arrangement of the micro-particles of the biocidal agent contained in the body of the medical device 1 can be uniform or non-uniform internally thereof. For example, the micro-particles of biocidal agent can be distributed, non-limitingly, such that the concentration thereof diminishes proceeding from inside towards outside of the body of the device 1: for example the particles are substantially concentrated at or in proximity of the external surface of the body of the medical device 1.

The biocidal agent preferably comprises silver, silver salts, complex silver compounds, always however characterised by a very low and in any case insignificant solubility in water, for example lower than $10^{-1}$ gram/litre (with 1 atm, 20° C.), in particular less than $10^{-2}$ gram/litre (with 1 atm, 20° C.). More preferably still, the biocidal substance is silver zeolite.

The medical device 1 can further comprise surfactant agents having a detaching function present in a weight percentage comprised between 0.01 and 1.5%, in particular between 0.1 and 1.0%, still more in particular between 0.2 and 0.7%. In greater detail, the surfactants used are configured such as to reduce the adhesion of the device to the walls of the seating 6 and thus facilitate extraction of the medical device 1 from the housing seating in a case in which there is a need to remove the prosthetic structure or indeed the whole dental prosthetic system 2. The surfactant agents can comprise for example cationic surfactants, such as quaternary ammonium salts (for example benzalkonium chloride—BAC, and cetyltrimethylammonium bromide—CTAB) or anionic surfactants such as: soaps, sulphonic esters and sulphates and sulphonates (i.e. sodium lauryl sulphate—SLS, lauryl ethoxy eolphate—LES and alkyl benzene sulphonic acids—ABS) or non-ionic surfactants, such as: ethers and esters, such as sorbitan-monooleate, sorbitan-monostearate, sorbitan-monopalmitate and sorbitan-di-oleate—SPAN, or alkyl-polyglucosides—APG and polyethylene glycol p-(1,1,3,3-tetramethyl butyl)phenyl ether. The and polyethylene glycol p-(1,1,3,3-tetramethyl butyl)phenyl ether is marketed under the name of Triton X-100.

The distribution of the surfactant agent or agents can be uniform or not in the volume of the body of the device 1; in the case of non-uniform distribution, the concentration of the surfactant agent can for example increase proceeding from inside towards the surface of the body in such a way that there is a maximum concentration of surfactant at the surface, with a maximization of the detaching effect.

Other complementary substances can further be added to the medical device 1, for example excipients and/or colorants, as long as they are compatible with the use envisaged for the invention and compatible with the polymer matrix used. Compounds used as both natural and synthetic excipients can be selected for example from a group constituted by water, alcohol, oils, gelling agents, suspending agents, emulsioning agents, thickeners, inert powders, sweeteners, aromas, perfumes, preservatives.

The particular composition of the medical device 1 enables defining some physical and mechanical characteristics of the device. In greater detail, the body can comprise a resistance to traction comprised between 2.0 and 20.0 N/mm$^2$, in particular comprised between 7.0 and 16.0 N/mm$^2$, still more in particular comprised between 9.5 and 12.5 N/mm$^2$). The medical device further exhibits a surface hardness measured in Shore A values comprised between 1 and 200, preferably between 20 and 120, more preferably between 50 and 90.

In relation to the surface finishing, the average surface roughness of the medical device 1 is comprised between 0.01 and 0.1 µm, in particular between 0.02 and 0.08 µm, still more in particular between 0.025 and 0.05 µm.

The geometry and composition of the material are useful in defining a medical device 1 able to prevent bacterial proliferation and further enable an easy and rapid installation and removal of the medical device. As previously mentioned, the body of the medical device 1 is configured such as to essentially occupy the internal volume of the longitudinal housing seating 6. The fact that the medical device 1 is complementarily shaped to the housing seating 6 or indeed forced internally thereof makes extraction difficult. It is therefore advantageous to attribute to the device some physical and geometric characteristics useful for facilitating both the installation and the extraction. The presence of at least a surfactant agent surely facilitates a greater sliding ease of the body of the medical device 1 internally of the housing seating and substantially functions as a detacher. As well as the presence of detaching agents, the average surface hardness and roughness of the body of the device contribute to a greater fluency of the body of the device internally of the housing seating 6. In fact, the greater the hardness and the smoother the surface finishing of the body, the lower the friction developing between the device 1 and the seating 6 will be.

USE

The above-described device can be used in a forming method of a dental prosthetic system 2 on an implant 5 previously installed in a seating made in the bone tissue of a maxilla or mandible of a patient.

The method in question comprises following steps:
- associating to the implant 5 a dental product 3 or an abutment as described above, which comprises at least a housing seating 6 longitudinally extending substantially along the height of the dental product or abutment 11; in practice this step can comprise a relative positioning of the dental product or the abutment with respect to the implant in such a way that the portions 16 and 17 join to one another;
- inserting a fixing element 4 in the housing seating, by acting on the fixing element 4, blocking the abutment 11 to the implant 5; the blocking can occur by screwing the screw 4 on the implant 5 and causing the axial packing between the screw 4, implant 5 and abutment 11;
- inserting a medical device 1 of the above-described type in the longitudinal seating 6,
- in a case in which the abutment 11 and the aesthetic portion have been previously joined, applying a closing element 8 for closing the access opening 7 subsequently to the introduction of the fixing element 4 and the medical device 1 in the longitudinal housing seating 6; in practice, the medical device is arranged internally of the longitudinal housing seating 6 and interposed between the fixing element 4 and the closing element 8, substantially filling the whole seating; in a case in which the abutment 11 and the aesthetic portion 22 have not been precedingly united, the step of application of the closing element is replaced with a fixing step of the aesthetic portion 22 on the abutment 11 following the blocking of the fixing element 4 and the positioning of the medical device 1 internally of the longitudinal housing seating 6.

Note that before or after the insertion of the device in the longitudinal seating 6 a step of polymerising the body of the medical device 1 can be included.

Also described in a method for maintaining a prosthetic system of the above-described type, Starting from a dental prosthetic system 2 installed at a seating made in the bone structure of a maxilla or a mandible of a patient, the following steps can be performed:
- removing the closing element 8 and/or the aesthetic portion 22,
- extracting the medical device 1,
- intervening on or replacing the fixing element 4,
- inserting a new medical device 1 of the above-described type into the longitudinal seating 6,
- applying a new closing element 8 and/or a new aesthetic portion (sometimes the aesthetic portion previously used can be re-utilised) such as to seal the seating 6 following the introduction of the fixing element 4 and the new medical device 1 in the longitudinal housing seating 6; in a case where the closing element 8 is present, the new medical device 1 is arranged internally of the longitudinal housing seating 6 and is interposed between the fixing element 4 and the closing element 8, while in a case in which an aesthetic portion 22 is present, the medical device 1 is interposed between the fixing element 4 and the aesthetic portion 22.

The medical device 1 is extremely useful during the step of removal of the closing element 8 or a step of perforation of the aesthetic portion 22 as it acts as a spacer with respect to the head of the screw 4, preventing the screw from being damaged during the removal of the closing element 8 or the perforation of the aesthetic portion 22. Further the device 1 is easily extractable and, in some embodiments, able to maintain substantially sterile the environment of the seating 6.

Lastly a method is described for removing the connecting element 11 of a dental prosthetic system 2, which is installed at a seating made in the bone tissue of a maxilla or mandible of a patient. The method comprises following steps:
- removing the closing element 8 or the aesthetic portion 22,
- extracting the medical device 1,
- disengaging the fixing element 4,
- separating the connecting element 11 from the implant 5.

As described or the maintenance method, the medical device 1 prevents damage to the head of the screw 4, is easily extractable and prevents bacterial proliferation.

ADVANTAGES OF THE INVENTION

The medical device 1 of the present invention exhibits one or more of the following advantages. The medical device 1 enables maintaining the housing longitudinal seating 6 of the dental prosthetic system impervious, thus preventing any penetration therein of cement or obturating materials, either provisional or definitive. The device further enables reducing the bacterial proliferation. Further, the medical device 1 enables resolving one or more of the following problems:
- it prevents the closing element 8 (cement), used for fixing the dental product 3 to the abutment, penetrating into the housing seating 6;
- it prevents penetration of the compound used for obturating the external end of the housing seating 6 in the case of dental products 3 directly screwed on the implant;
- it leaves no residues once removed and is easily removable;
- it practically annuls the possibility of adhesion and proliferation of bacteria internally of the housing seating, and further guarantees maximum resistance to chewing stress;
- it eliminates the unpleasant odour that bacteria usually emit when trapped in the housing seating.

The invention claimed is:

1. A method of forming a dental prosthetic system on an implant previously installed in a seating made in the bone tissue of a maxilla or a mandible of a patient, the method comprising the following steps:
   associating to the implant at least one of a dental product and a connecting element, the dental product or the connecting element comprising at least a longitudinal housing seating extending substantially along a height of the dental product or respectively along a height of the connecting element,
   inserting a fixing element in the longitudinal housing seating and, by acting on the fixing element, blocking the dental product or respectively the connecting element to the implant,
   inserting in the longitudinal housing seating a medical device comprising a preformed solid body having a predetermined volume and an elongate conformation, and
   axially blocking the medical device in the longitudinal housing seating subsequently to the introduction of the fixing element, wherein the solid body comprises an active agent selected from the group consisting of: a biocidal agent, an antibacterial agent, an antiviral agent, and a bacteriostatic agent, wherein the active agent is present at a weight percentage comprised between 0.1 and 5%.

2. The method of claim 1, wherein the step of axially blocking comprises applying a closing element to an access opening of the longitudinal seating present on the dental product or the connecting element, the application occurring subsequently to the introduction of the fixing element and the medical device in the longitudinal housing seating, the medical device being arranged internally of the longitudinal housing seating and interposed between the fixing element and the closing element.

3. The method of claim 2, further comprising following steps:
   removing the closing element,
   extracting the medical device,
   intervening on or replacing the fixing element,
   inserting a new medical device into the longitudinal seating, and
   applying a new closing element to axially block the new medical device in the longitudinal housing seating subsequently to a reintroduction of the fixing element, the new medical device being arranged internally of the longitudinal housing seating, interposed between the fixing element and the new closing element.

4. The method of claim 2, wherein the solid body of the medical device occupies both the axial dimension and the transversal dimension of the longitudinal housing seating.

5. The method of claim 1, wherein the step of axially blocking comprises cementing an aesthetic portion to the connecting element subsequently to the introduction of the fixing element and the medical device in the longitudinal housing seating, the medical device being arranged internally of the longitudinal housing seating and interposed between the fixing element and the aesthetic portion.

6. The method of claim 5, further comprising following steps:
   removing the aesthetic portion,
   extracting the medical device,
   intervening on or replacing the fixing element,
   inserting a new medical device into the longitudinal seating, and
   applying a new aesthetic portion such as to axially block the new medical device in the longitudinal housing seating subsequently to a reintroduction of the fixing element, the new medical device being arranged internally of the longitudinal housing seating, interposed between the fixing element and the new aesthetic portion.

7. The method of claim 1, wherein:
   (i) the solid body of the medical device comprises polymer or polymerisable material in a weight percentage comprised between 80 and 99.5%;
   (ii) the method comprises a step of polymerisation of the polymerisable material in the solid body of the medical device, the polymerisation step being carried out before or after the inserting of the medical device into the longitudinal seating;
   or both (i) and (ii).

8. The method of claim 1, wherein the active agent is structured in micro-particles, dimensions of which are comprised between 0.5 and 30 μm, and wherein the active agent comprises at least one of: silver, silver salts, silver-based compounds, and silver zeolite.

9. The method of claim 1, wherein the active agent contained in the solid body of the medical device is arranged in a non-uniform way internally of the medical device, the active agent exhibiting a growing concentration proceeding from inside towards an external surface of the solid body of the medical device.

10. The method of claim 1, wherein the solid body of the medical device comprises internally of the composition thereof, at least a surfactant agent with a detaching function, wherein the surfactant agent is present with a weight percentage comprised between 0.01 and 1.5% and is at least one selected from a group consisting of:
    a cationic surfactant,
    an anionic surfactant, and
    a non-ionic surfactant.

11. The method of claim 10, wherein the surfactant agent is present in the solid body of the device with a growing concentration proceeding from inside towards an external surface of the solid body of the medical device.

12. The method of claim 1, wherein the material constituting the body of the medical device exhibits:
    a resistance to traction comprised between 2.0 and 20.0 $N/mm^2$, and
    a surface hardness value measured in Shore A comprised between 1 and 200, and
    wherein the body of the medical device exhibits an average surface roughness comprised between 0.01 and 0.1 μm.

13. The method of claim 1, wherein the solid body extends along a prevalent development direction, and wherein the ratio between the extension of the body along the prevalent development direction and the maximum transversal dimension of the body, measured perpendicularly with respect to the prevalent development direction, is greater than 2.

14. The method of claim 1, wherein the solid body of the medical device comprises a recess developing substantially parallel to the prevalent development direction of the body, wherein the recess delimits an opening on the surface of the body of the medical device,
    wherein the opening of the recess exhibits a width, measured transversally to the prevalent direction, that is linearly variable along the development of the body or constant along the development of the body, and
    further wherein the recess exhibits, in transversal section, a substantially V-shaped profile in which a point of the V is facing towards an inside of the body, or wherein the recess exhibits in transversal section a substantially C-shaped profile in which the concavity of the C is facing towards an outside of the body.

15. The method of claim 1, wherein the longitudinal housing seating exhibits a substantially truncoconical or cylindrical or prismatic shape, and wherein the medical device when installed in the longitudinal housing seating is complementarily shaped to the longitudinal housing seating.

16. The method of claim 1, wherein the dental product comprises an aesthetic portion engaged to the connecting element and defining the external part of the dental product, the aesthetic portion at least partly cladding the connecting element, the housing seating being defined internally of the connecting element and/or the aesthetic portion, wherein the connecting element exhibits a first portion, unremovably engaged to the aesthetic portion, and a second portion removably engaged to the implant via the fixing element having an active terminal portion inserted in and coupled with a corresponding seating provided in the implant.

17. The method of claim 16, wherein the longitudinal housing develops over at least a preponderant part thereof internally of the connecting element, wherein a terminal part of the longitudinal housing seating also extends beyond the connecting element into a part of the aesthetic portion of the dental product.

18. The method of claim 1, wherein the active agent is structured in micro-particles, dimensions of which are comprised between 0.5 and 30 μm, and wherein the active agent comprises silver zeolite.

19. A method of forming a dental prosthetic system on an implant previously installed in a seating made in the bone tissue of a maxilla or a mandible of a patient, the method comprising the following steps:
- associating to the implant at least one of a dental product and a connecting element, the dental product or the connecting element comprising at least a longitudinal housing seating extending substantially along a height of the dental product or respectively along a height of the connecting element,
- inserting a fixing element in the longitudinal housing seating and, by acting on the fixing element, blocking the dental product or respectively the connecting element to the implant,
- inserting in the longitudinal housing seating a medical device comprising a preformed solid body having a predetermined volume and an elongate conformation, and
- axially blocking the medical device in the longitudinal housing seating subsequently to the introduction of the fixing element.

20. A method of forming a dental prosthetic system on an implant previously installed in a seating made in the bone tissue of a maxilla or a mandible of a patient, the method comprising the following steps:
- associating to the implant at least one of a dental product and a connecting element, the dental product or the connecting element comprising at least a longitudinal housing seating extending substantially along a height of the dental product or respectively along a height of the connecting element,
- inserting a fixing element in the longitudinal housing seating and, by acting on the fixing element, blocking the dental product or respectively the connecting element to the implant,
- inserting in the longitudinal housing seating a medical device comprising a preformed solid body having a predetermined volume and an elongate conformation,
- axially blocking the medical device in the longitudinal housing seating subsequently to the introduction of the fixing element,
- wherein the solid body of the medical device comprises a recess developing substantially parallel to the prevalent development direction of the body, wherein the recess delimits an opening on the surface of the body of the medical device,
- wherein the opening of the recess exhibits a width, measured transversally to the prevalent direction, that is linearly variable along the development of the body or constant along the development of the body, and
- further wherein the recess exhibits, in transversal section, a substantially V-shaped profile in which a point of the V is facing towards an inside of the body, or wherein the recess exhibits in transversal section a substantially C-shaped profile in which the concavity of the C is facing towards an outside of the body.

* * * * *